(12) United States Patent
Nayet et al.

(10) Patent No.: US 8,702,713 B2
(45) Date of Patent: Apr. 22, 2014

(54) INSTRUMENTS AND TECHNIQUES FOR ADJUSTING RELATIVE POSITIONING OF BONES OR BONY TISSUES

(75) Inventors: Jerome Nayet, Saint Genis Pouilly (FR); Bertrand Peultier, Les Hopitaux Neufs (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 426 days.

(21) Appl. No.: 13/014,097

(22) Filed: Jan. 26, 2011

(65) Prior Publication Data

US 2012/0191143 A1   Jul. 26, 2012

(51) Int. Cl.
*A61B 17/70* (2006.01)

(52) U.S. Cl.
USPC ...................................... 606/86 A

(58) Field of Classification Search
USPC ....... 606/246–251, 257, 279, 277, 278, 86 R, 606/90, 105, 86 A
See application file for complete search history.

(56) References Cited

U.S. PATENT DOCUMENTS

| | | | |
|---|---|---|---|
| 1,920,821 A | | 8/1933 | Wasswnarr |
| 3,244,170 A | * | 4/1966 | Mcelvenny ...................... 606/71 |
| 5,989,251 A | * | 11/1999 | Nichols .......................... 606/250 |
| 2005/0245928 A1 | | 11/2005 | Collearn et al. |
| 2008/0088266 A1 | | 3/2008 | Dierich et al. |
| 2009/0062857 A1 | | 3/2009 | Ramsay et al. |
| 2010/0324610 A1 | | 12/2010 | Bridwell et al. |

FOREIGN PATENT DOCUMENTS

| | | |
|---|---|---|
| DE | 38 07 346 C1 | 6/1989 |
| EP | 0 159 007 B1 | 11/1989 |
| EP | 0 316 371 B1 | 10/1991 |
| EP | 0 528 177 A2 | 7/1992 |
| WO | 90 02527 A1 | 3/1990 |
| WO | 2004014231 A1 | 2/2004 |
| WO | 2005009209 A2 | 2/2005 |
| WO | 200605822 A2 | 6/2006 |
| WO | 2006094754 A1 | 9/2006 |
| WO | 2006118998 A1 | 11/2006 |
| WO | 2007092797 A2 | 8/2007 |
| WO | 2008155772 A1 | 12/2008 |
| WO | 2010099478 A1 | 9/2010 |

* cited by examiner

*Primary Examiner* — Pedro Philogene
*Assistant Examiner* — David Comstock
(74) *Attorney, Agent, or Firm* — Sorell Lenna & Schmidt LLP

(57) ABSTRACT

Systems, methods, devices and instruments for adjusting the relative positioning of bones or bony tissues, such as two or more vertebrae, are provided. More particularly, in one form, an instrument includes first and second end members that are freely movable relative to one another in a first configuration of the instrument, while in a second configuration the first and second end members are only movable relative to one another upon rotation of a displacement member. In one aspect of this and/or other forms, the first and second end members include hook portions that are selectively rotatable relative to one another such that the instrument can be used for compression or distraction of the bones or bony tissues. In another form, techniques for adjusting the relative positioning of bones or bony tissues are provided.

14 Claims, 12 Drawing Sheets

INSTRUMENTS AND TECHNIQUES FOR ADJUSTING RELATIVE POSITIONING OF BONES OR BONY TISSUES

BACKGROUND

The present application relates to instrumentation and techniques useful in orthopedic surgery, and in particular to instrumentation useful in compressing, distracting or otherwise adjusting the relative positioning of bones or bony tissues, one non-limiting example of which includes vertebrae of the spinal column.

A variety of spinal injuries and deformities can occur due to trauma, disease, or congenital effects. These injuries and diseases can, ultimately, result in the misalignment of two or more vertebrae of the spinal column which may cause pain or other discomfort. Correction of such misalignment is often addressed by surgical procedures which utilize one or more interbody implants, plates, tethers, cables and/or rods to hold the vertebrae in a corrected orientation achieved by moving the vertebrae during the surgical procedure.

Several types of tools for moving vertebrae or other bones into a desired orientation during surgery to address trauma or correct abnormalities are known. Among these include instruments that use cables to pull together bones or artificial implants placed in such bones, scissor-like tools that apply leverage around a central fulcrum to move bones or implants toward or away from each other, and even the surgeon's own hands. Such manipulations or adjustments of bones are indicated for correction of a number of orthopedic conditions. For example, in the case of a scoliosis or other abnormal positioning of the spine, one or more vertebrae or vertebral segments may require compression or distraction with respect to adjacent bones to achieve a better or more normal position. In the case of a trauma, for example, after an injury to a bone or adjacent tissue or removal of a cancerous or other mass, compression or distraction of tissue may be required to induce proper healing, to accommodate a therapy such as implantation of spacing or holding devices or of therapeutic material (e.g. bone morphogenic protein (BMP), allograft, autograft or other osteogenic substances, or medications), or for other reasons. Prior compression and/or distraction tools can be difficult, awkward and/or time consuming to use in certain surgical pathologies or situations. In addition, the utility of some instruments can be limited to performing only one aspect of a surgical procedure. Thus, there remains a need in the art for such instruments that provided advantages over existing tools.

SUMMARY

Instruments, systems, methods and devices for adjusting the relative position of bones or bony tissues, such as two or more vertebrae of the spinal column, are provided. More particularly, in one form, an instrument includes first and second end members that are freely movable relative to one another in a first configuration of the instrument, while in a second configuration of the instrument the first and second end members are only movable relative to one another upon rotation of a displacement member. In one aspect of this and/or other forms, the first and second end members include hook portions which are selectively rotatable relative to one another such that the instrument can be used for compression or distraction of the bones or bony tissues as appropriate. In another form, techniques for adjusting the relative positioning of bones or bony tissues are provided. However, different forms and applications are also envisioned.

In one embodiment, an instrument for adjusting relative positioning of at least two vertebrae includes a first end member including a guide bar and a displacement member extending therefrom. The instrument also includes a second end member that is configured to engage with the guide bar and the displacement member and includes an engaging member that is selectively engageable with the displacement member. The second end member is movable relative to the first end member along the guide bar and the displacement member upon rotation of the displacement member relative to the first end member when the engaging member is engaged with the displacement member and independent of rotation of the displacement member relative to the first end member when the engaging member is disengaged from the displacement member.

In another embodiment, an instrument for adjusting relative positioning of at least two vertebrae includes a first end member and a second end member axially displaceable relative to the first end member. The first and second end members each include a hook member including an engaging portion configured to engage with a respective one of a first anchor extender and a second anchor extender. In addition, each of the hook members is selectively rotatable relative to a respective one of the first and second end members from a first position where the engaging portions face one another to a second position where the engaging portions face away from one another.

In yet another embodiment, a system for adjusting relative positioning of at least two vertebrae includes a first anchor extender extending between a proximal end and a distal end configured to engage with a first bone anchor and a second anchor extender extending between a proximal end and a distal end configured to engage with a second bone anchor. The system also includes a first instrument including a first end member engageable with the proximal end of the first anchor extender and a second end member engageable with the proximal end of the second anchor extender. The second end member of the first instrument is selectively movable relative to the first end member to change a distance between the proximal ends of the anchor extenders. A second instrument also included in the system includes a first end member and a second end member selectively movable relative to the first end member to change a distance between the first and second end members. Further, the second instrument is engageable with the first and second anchor extenders at a location between the proximal and distal ends.

In a further embodiment, techniques for adjusting the relative positioning of bones or bony tissues, such as two or more vertebrae, are provided. In one aspect, these techniques include engaging first and second anchor extenders to bone anchors engaged with first and second vertebrae, respectively, and engaging one or more instruments with the anchor extenders to adjust the positioning of the vertebrae through manipulation of the one or more instruments.

Other embodiments include unique methods, systems, devices, kits, assemblies, equipment, and/or apparatus for use in connection with the stabilization, support, manipulation, alignment or correction of two or more vertebrae. However, in other embodiments, different forms and applications are also envisioned.

Further embodiments, forms, features, aspects, benefits, objects and advantages of the present application will become apparent from the detailed description and figures provided herewith.

DESCRIPTION OF THE ILLUSTRATED EMBODIMENTS

Figure 1:
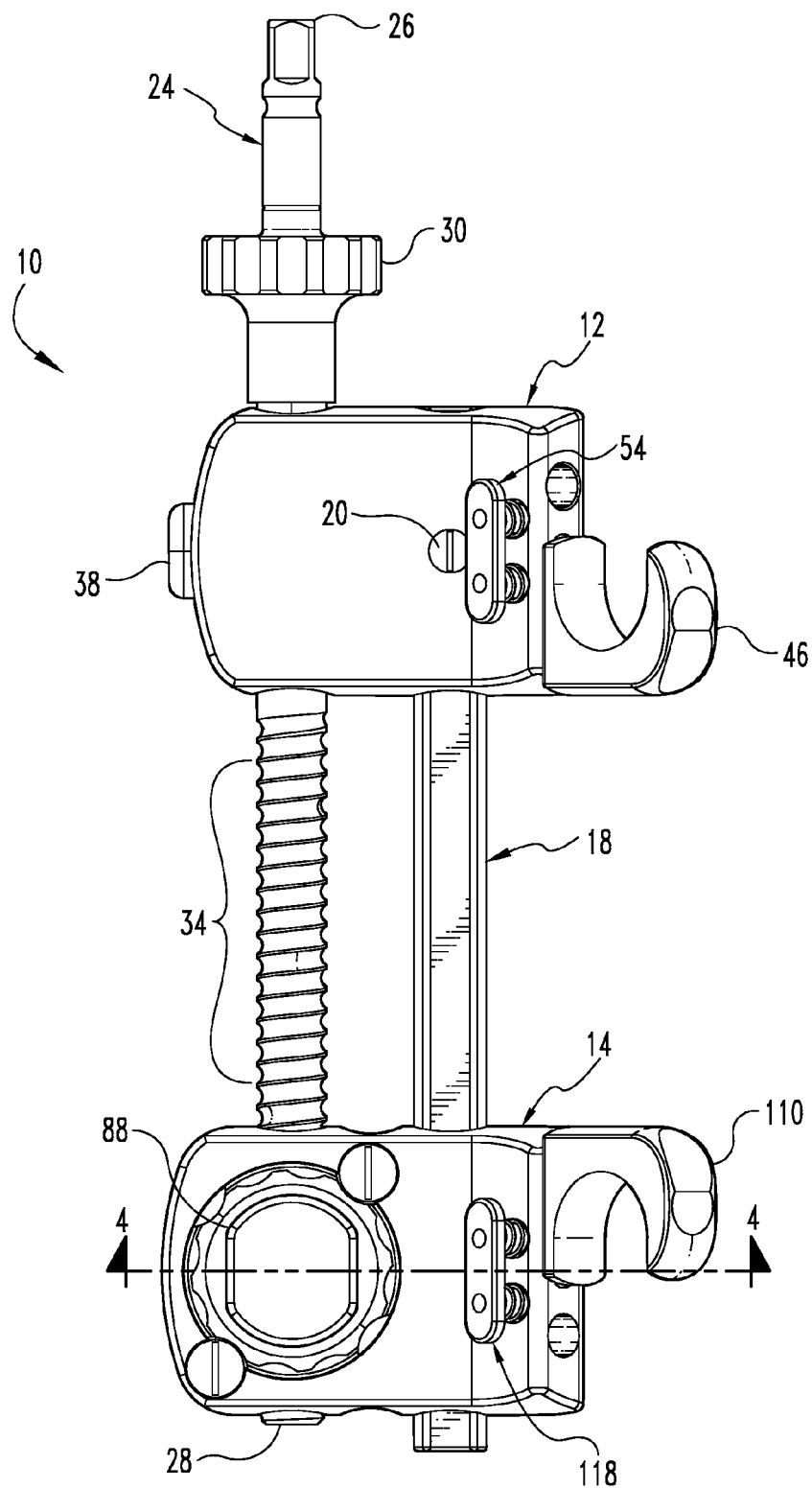
FIG. 1 is a top plan view of a first surgical instrument.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices and described methods, and any such further applications of the principles of the invention as illustrated herein are contemplated as would normally occur to one skilled in the art to which the invention relates.

Systems, methods, devices and instruments for adjusting the relative position of bones or bony tissues, such as two or more vertebrae, are provided. More particularly, in one form, an instrument includes first and second end members that are freely movable relative to one another in a first configuration of the instrument, while in a second configuration of the instrument the first and second end members are only movable relative to one another upon rotation of a displacement member. In one aspect of this and/or other forms, the first and second end members include hook portions which are selectively rotatable relative to one another such that the instrument can be configured for compression or distraction of the bones or bony tissues as appropriate. In another form, techniques for adjusting the relative positioning of bones or bony tissues are provided. It should be appreciated that alternative forms, aspects, configurations, arrangements and methods are contemplated with respect to the subject matter disclosed, described and claimed herein.

Figure 2:
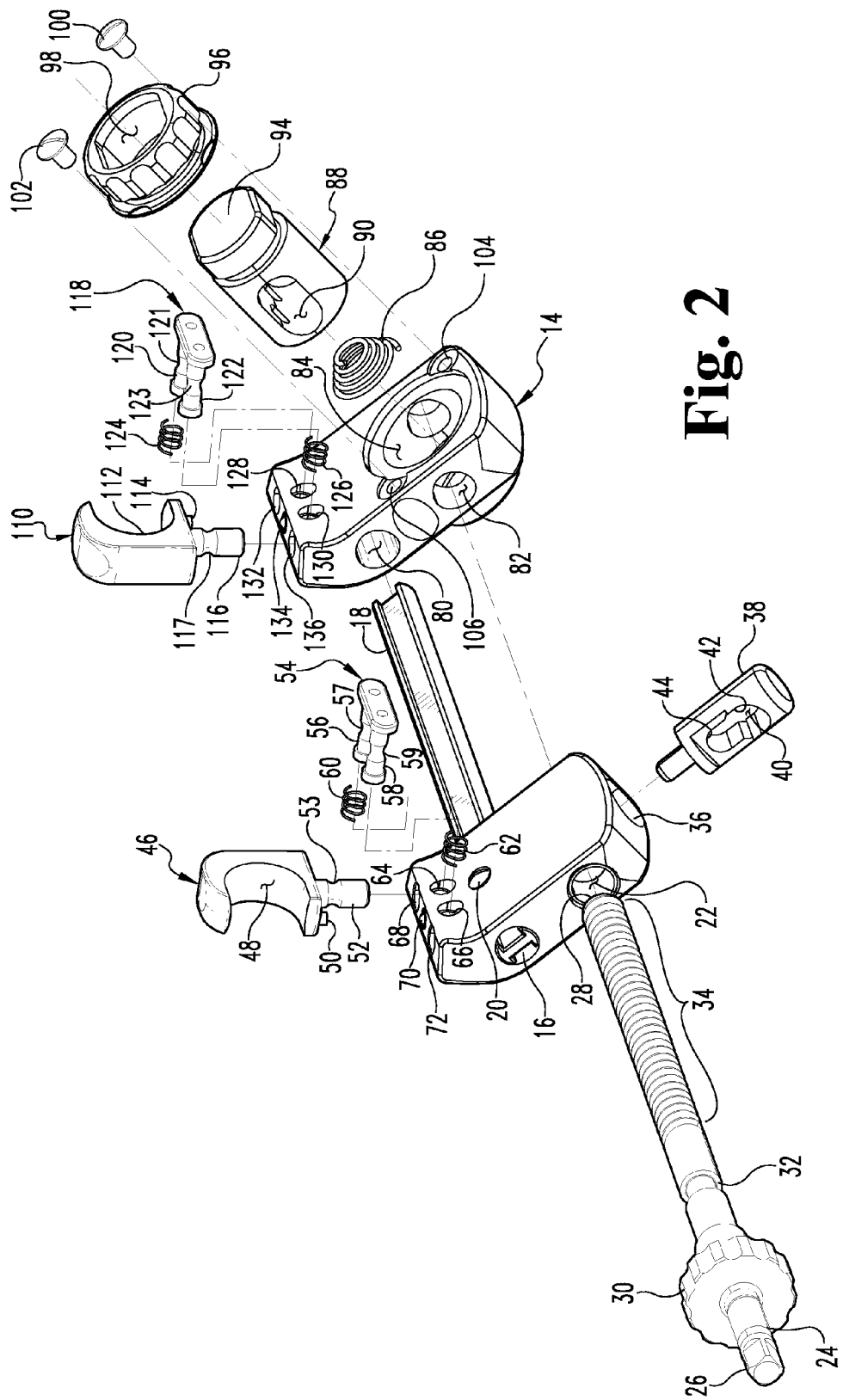
FIG. 2 is an exploded perspective view of the surgical instrument illustrated in FIG. 1.

Referring generally to FIGS. 1-5, illustrated therein is an instrument 10 configured for adjusting the relative positioning of bones or bony tissues. The instrument 10 includes a first end member 12 and a second end member 14 that is movable relative to the first end member 12, further details of which will be provided below. As illustrated in FIG. 2, the first end member 12 includes a first passage 16 in which an elongated guide bar 18 is positioned such that the guide bar 18 extends from the first end member 12 for engagement with the second end member 14. A retaining member 20, such as a threaded fastener, extends through a transverse bore (not shown) and into engagement with the guide bar 18 in order to couple the first end member 12 with the guide bar 18. In the illustrated embodiment, the guide bar 18 includes a generally I-shaped cross-sectional profile with the opposite ends thereof including an arcuate or semi-circular configuration. However, it should be appreciated that other cross-sectional profiles for the guide bar 18 are contemplated and fall within the scope of the subject disclosure.

The first end member 12 also includes a second passage 22 through which a displacement member 24 is positioned such that the displacement member 24 also extends from the first end member 12 in the same direction as the guide bar 18 also for engaging with the second end member 14, further details of which will be provided below. As illustrated in FIG. 1, the guide bar 18 and the displacement member 24 extend from the first end member 12 in a parallel or substantially parallel arrangement relative to one another. The displacement member 24 generally extends between a first end 26 and a second end 28. In the illustrated form, the first end 26 has a generally square configuration configured to facilitate engagement with one or more other surgical instruments, one non-limiting example of which includes a driver instrument. However, in other non-illustrated forms, it is contemplated that the first end 26 could be provided with a round or circular configuration and/or otherwise not be configured to facilitate engagement with any other surgical instruments.

The displacement member 24 also includes a handle member 30, a reduced diameter portion 32 and an externally threaded portion 34. In the illustrated form, the externally threaded portion 34 extends along a portion of the displacement member 24 from the second end 28 toward the first end 26. In addition, the handle member 30 is positioned adjacent to the first end 26 and is generally configured for engagement by a user to facilitate rotation of the displacement member 24. The reduced diameter portion 32 is positioned between the handle member 30 and the externally threaded portion 34 such that it is positioned in the first end member 12 when the displacement member 24 is positioned in the passage 22. More particularly, when the displacement member 24 is positioned in the passage 22, the reduced diameter portion 32 is generally aligned with a transverse bore 36 that extends in communication with the passage 22. The first end member 12 also includes a coupling member 38 that is configured to be positioned in the transverse bore 36 and to couple the first end member 12 with the displacement member 24. More particularly, the coupling member 38 generally includes a passage 40 that has a first portion 42 and a second portion 44 that has a reduced profile relative to the first portion 42. In this arrangement, the first portion 42 is generally configured to allow the displacement member 24 to freely slide through the coupling member 38 while the second portion 44 is generally configured to engage with the reduced diameter portion 32 of the displacement member 24 to prevent movement of the displacement member 24 through the coupling member 38.

The first end member 12 also includes a biasing element that engages with the coupling member 38 when positioned in the transverse bore 36. Similarly, in this arrangement, the coupling member 38 can be depressed to overcome the force of the biasing element such that the first portion 42 of the passage 40 of the coupling member 38 is aligned with the passage 22 and the displacement member can be passed through the passages 22, 40. Once the displacement member 24 is appropriately positioned in the passage 22 such that the reduced diameter portion 32 is generally aligned with the transverse bore 36, the coupling member 38 can be released such that the biasing element forces the second portion 44 of the passage 40 into engagement with the reduced diameter portion 32. In this arrangement, engagement of the second portion 44 with the reduced diameter portion 32 axially fixes the displacement member 24 relative to the first end member 12 while allowing rotation of the displacement member 24 relative to the first end member 12. Similarly, when the displacement member 24 is engaged by the coupling member 38, rotation of the handle member 30 will result in rotation of the displacement member 24, including the externally threaded portion 34, relative to the first end member 12.

The second end member 14 generally includes a passage 80 configured to receive a portion of the guide bar 18, and a passage 82 generally configured to receive a portion of the externally threaded portion 34 of the displacement member 24. The second end member 14 also includes a receptacle 84 through which the passage 82 transversely extends. The receptacle 84 generally receives a biasing member 86 which, in the illustrated form, is a coil spring. However, it should be appreciated that other configurations for the biasing member 86 are contemplated. The receptacle 84 also receives an engaging member 88 that is selectively engageable with the externally threaded portion 34 of the displacement member 24, further details of which will be provided below. The second end member 14 also includes a cap member 96 that includes a hollow interior 98 configured to be positioned around a user engagement portion 94 of the engaging member 88. A pair of retaining elements 100, 102, such as threaded fasteners, are received in corresponding receptacles 104, 106 formed in the second end member 14 in order to couple the cap member 96 with the second end member 14 and retain the engaging member 88 and the biasing member 86 in the receptacle 84. When retained in the receptacle 84, the biasing member 86 generally forces the engaging member 88 away from the bottom of the receptacle 84 and toward the cap member 96.

Figure 4:
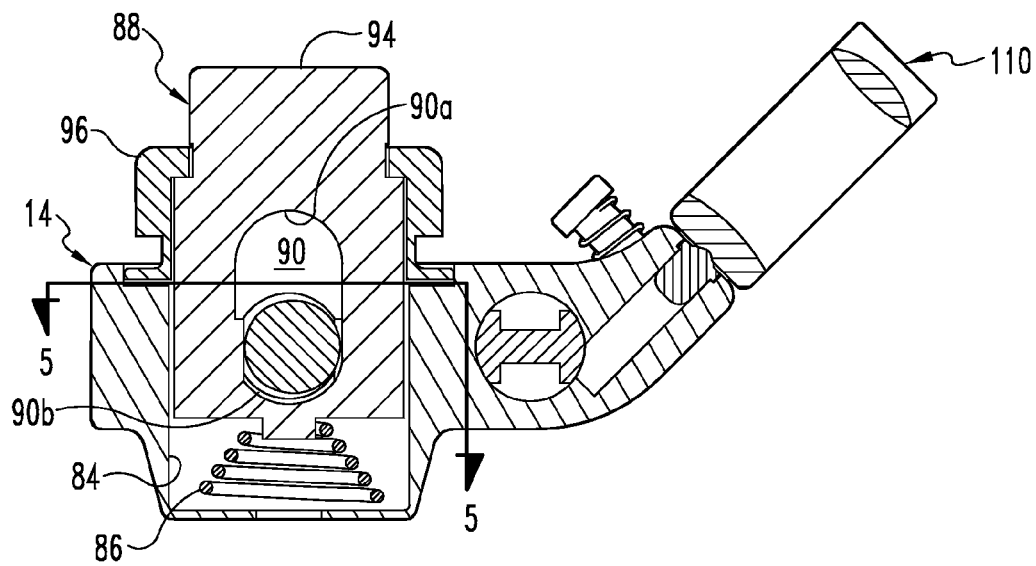
FIG. 4 is a cross sectional view of FIG. 1 taken along line 4-4 of FIG. 1.
Figure 5:
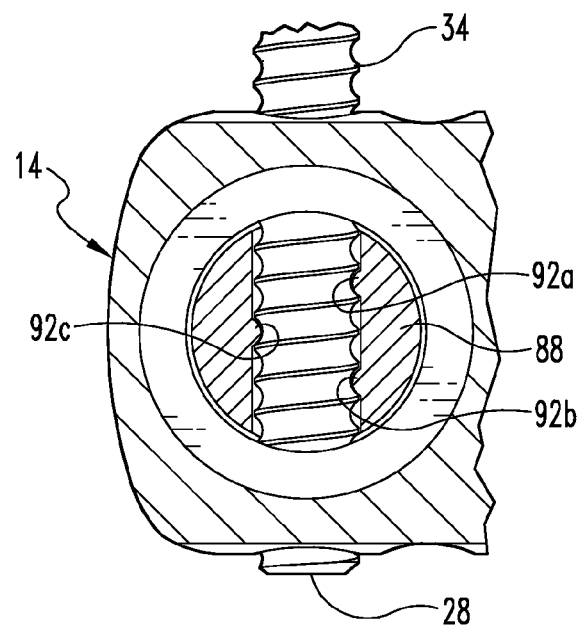
FIG. 5 is a cross sectional view of FIG. 4 taken along line 5-5 of FIG. 4.

As indicated above, the engaging member 88 is generally configured to engage with the externally threaded portion 34 of the displacement member 24. More specifically, the engaging member 88 includes an elongated passage 90 that includes an upper portion 90a positioned opposite of a lower portion 90b, as shown in FIG. 4. The upper portion 90a generally does not engage with the displacement member 24 when it is positioned in the upper portion 90a such that the displacement member 24 may freely pass through the engaging member 88. Similarly, when the externally threaded portion 34 of the displacement member 24 is positioned in the upper portion 90a of the passage 90, the engaging member 88 will generally be freely movable along the longitudinal axis of the displacement member 24. In contrast to the upper portion 90a, the lower portion 90b of the passage 90 includes a plurality of rounded projections 92a-c configured to engage with threading of the externally threaded portion 34 of the displacement member 24 when it is positioned in the lower portion 90b of the passage 90. When the externally threaded portion 34 of the displacement member 24 is positioned in the lower portion 90b of the passage 90, rotation of the displacement member 24 will result in displacement of the second end member 14 along the longitudinal axes of the displacement member 24 and the guide bar 18.

In its normal operating configuration, the biasing member 86 generally forces the engaging member 88 toward the cap member 96 such that the externally threaded portion 34 of the displacement member 24 is positioned in the lower portion 90b of the passage 90 of the engaging member 88. In this arrangement, the rounded projections 92a-c engage with the externally threaded portion 34 and the distance between the first and second end members 12, 14 can be adjusted by rotating the displacement member 24. However, a user may also engage the user engagement portion 94 of the engaging member 88 to depress the biasing member 86 such that the externally threaded portion 34 of the displacement member 24 is positioned in the upper portion 90a of the passage 90 of the engaging member 88 and the second end member 14 can be freely moved along the displacement member 24 and the guide bar 18 relative to the first end member 12 without rotation of the displacement member 24. Once a desired relationship between the first and second end members 12, 14 has been obtained, the user engagement portion 94 of the engaging member 88 can be released such that the externally threaded portion 34 is again positioned in the lower portion 90b and engaged by the rounded projections 92a-c, thereby preventing displacement of the first and second end members 12, 14 relative to one another unless the displacement member 24 is correspondingly rotated.

While not previously discussed, it should be appreciated that each of the first and second end members 12, 14 also includes a hook portion 46, 110, respectively. In the illustrated form, the hook portions 46, 110 are generally configured to engage with an anchor extender or another instrument that is engaged with a bone anchor, although it should be appreciated that in this and/or other forms the hook portions 46, 110 may be directly engaged with bones or bony tissues. The hook portion 46 generally has a U-shaped configuration that defines an engaging portion 48. The hook portion 46 also includes first and second stems 50, 52 extending therefrom. As illustrated in FIG. 2, the second stem 52 includes a concave, radial groove 53 formed therein. As also illustrated in FIG. 2, the first end member 12 includes apertures 68, 70, 72 which generally face in a partially upward and lateral direction such that the apertures are generally obliquely oriented relative to the longitudinal axes of the guide bar 18 and the displacement member 24. The aperture 70 is configured to receive the stem 50 and the apertures 68, 72 are configured to receive the stem 52. In this arrangement, the hook portion 46 can be rotated relative to the first end member 12 between a first configuration where the engaging portion 48 faces away from the second end member 14 with the stems 50, 52 positioned in the apertures 70, 68, respectively, and a second configuration where the engaging portion 48 faces toward the second end member 14 with the stems 50, 52 positioned in the apertures 70, 72, respectively.

Figure 3:
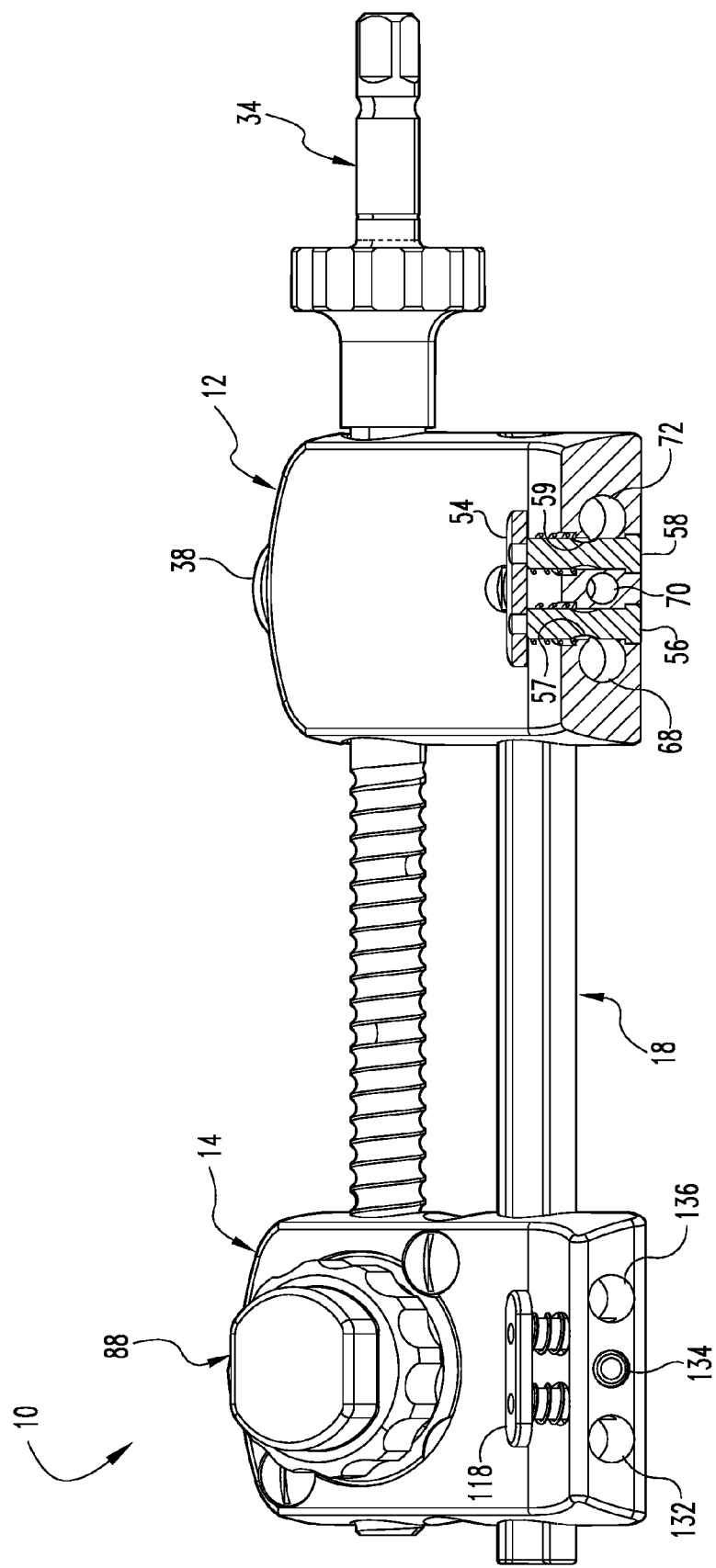
FIG. 3 is a side view of the surgical instrument illustrated in FIG. 1 with certain features shown in cross section.

In addition to the foregoing, the first end member 12 also includes a release member 54 that includes a first stem 56 and a second stem 58. As illustrated in FIG. 2, the first stem 56 includes a concave, radial groove 57 and the second stem 58 includes a concave, radial groove 59. The first end member 12 also includes a receptacle 64 configured to receive the first stem 56 and a biasing element 60, and a receptacle 66 configured to receive the second stem 58 and a biasing element 62. In this arrangement, the release member 54 is normally biased relative to the first end member 12 such that the grooves 57, 59 are generally positioned above the apertures 68, 72, as shown in FIG. 3. Similarly, when the hook portion 46 is engaged with the first end member 12, the stem 50 is positioned in the aperture 70, and the stem 52 is positioned in one of the apertures 68, 72, the hook portion 46 will be retained in engagement with the first end member 12 by the release member 54. However, if it is desired to change the orientation of the hook portion 46 relative to the first end member 12, the release member 54 can be depressed such that the radial grooves 57, 59 are brought into alignment with the apertures 68, 72. Once positioned in this manner, one of the grooves 57, 59 (depending on which one of the apertures 68, 72 the stem 52 is positioned in) will become aligned with the groove 53 on the stem 52 and allow the hook portion 46 to be removed from the first end member 12. The orientation of the hook portion 46 can then be changed, the stem 50 can be inserted into the aperture 70, and the stem 52 can be inserted into an appropriate one of the apertures 68, 72 to reengage the hook portion 46 with the first end member 12. Once the hook portion 46 is reengaged with the first end member 12, the release member 54 can be released such that it is again biased away from the first end member 12 with the grooves 57, 59 positioned above the apertures 68, 72 in order to prevent removal of the hook portion 46 from the first end member 12.

The hook portion 110 generally has a U-shaped configuration that defines an engaging portion 112. The hook portion 110 also includes first and second stems 114, 116 extending therefrom. As illustrated in FIG. 2, the second stem 116 includes a concave, radial groove 117 formed therein. As also illustrated in FIG. 2, the second end member 14 includes apertures 132, 134, 136 which generally face in a partially upward and lateral direction such that the apertures are generally obliquely oriented relative to the longitudinal axes of the guide bar 18 and the displacement member 24. The aperture 134 is configured to receive the stem 114 and the apertures 132, 136 are configured to receive the stem 116. In this arrangement, the hook portion 110 can be rotated relative to the second end member 14 between a first configuration where the engaging portion 112 faces away from the first end member 12 with the stems 114, 116 positioned in the apertures 134, 136, respectively, and a second configuration where the engaging portion 112 faces toward the first end member 12 with the stems 114, 116 positioned in the apertures 134, 132, respectively.

The second end member 14 also includes a release member 118 that includes a first stem 120 and a second stem 122. As illustrated in FIG. 2, the first stem 120 includes a concave, radial groove 121 and the second stem 122 includes a concave, radial groove 123. The second end member 14 also includes a receptacle 128 configured to receive the first stem 120 and a biasing element 124, and a receptacle 130 configured to receive the second stem 122 and a biasing element 126. In this arrangement, the release member 118 is normally biased relative to the second end member 14 such that the grooves 121, 123 are generally positioned above the apertures 132, 136. Similarly, when the hook portion 110 is engaged with the second end member 14, the stem 114 is positioned in the aperture 134 and the stem 116 is positioned in one of the apertures 132, 136, the hook portion 110 will be retained in engagement with the second end member 14 by the release member 118. However, if it is desired to change the orientation of the hook portion 118 relative to the second end member 14, the release member 118 can be depressed such that the radial grooves 121, 123 are brought into alignment with the apertures 132, 136. Once positioned in this manner, one of the grooves 121, 123 (depending on which one of the apertures 132, 136 the stem 116 is positioned in) will become aligned with the groove 117 on the stem 116 and allow the hook portion 110 to be removed from the second end member 14. The orientation of the hook portion 110 can then be changed and the stem 114 can be inserted into the aperture 134 and the stem 116 can be inserted into an appropriate one of the apertures 132, 136 to reengage the hook portion 110 with the second end member 14. Once the hook portion 110 is reengaged with the second end member 14, the release member 118 can be released such that it is again biased away from the second end member 14 with the grooves 121, 123 being positioned above the apertures 132, 136 in order to prevent removal of the hook portion 110 from the second end member 14.

It should be appreciated that the hook portions 46, 110 can be adjusted relative to one another and the end members 12, 14 such that the instrument 10 can be used to compress or bring together bones or bony tissues and/or to distract or move the bones or bony tissues apart. More particularly, when the hook portions 46, 110 are arranged such that the engaging portions 48, 112 face away from one another as illustrated in FIG. 1, the instrument 10 can be used for distraction of bones or bony tissues. However, once the instrument is reconfigured such that the engaging portions 48, 112 face toward one another, the instrument 10 can be used for compression of bones or bony tissues.

Figure 6:
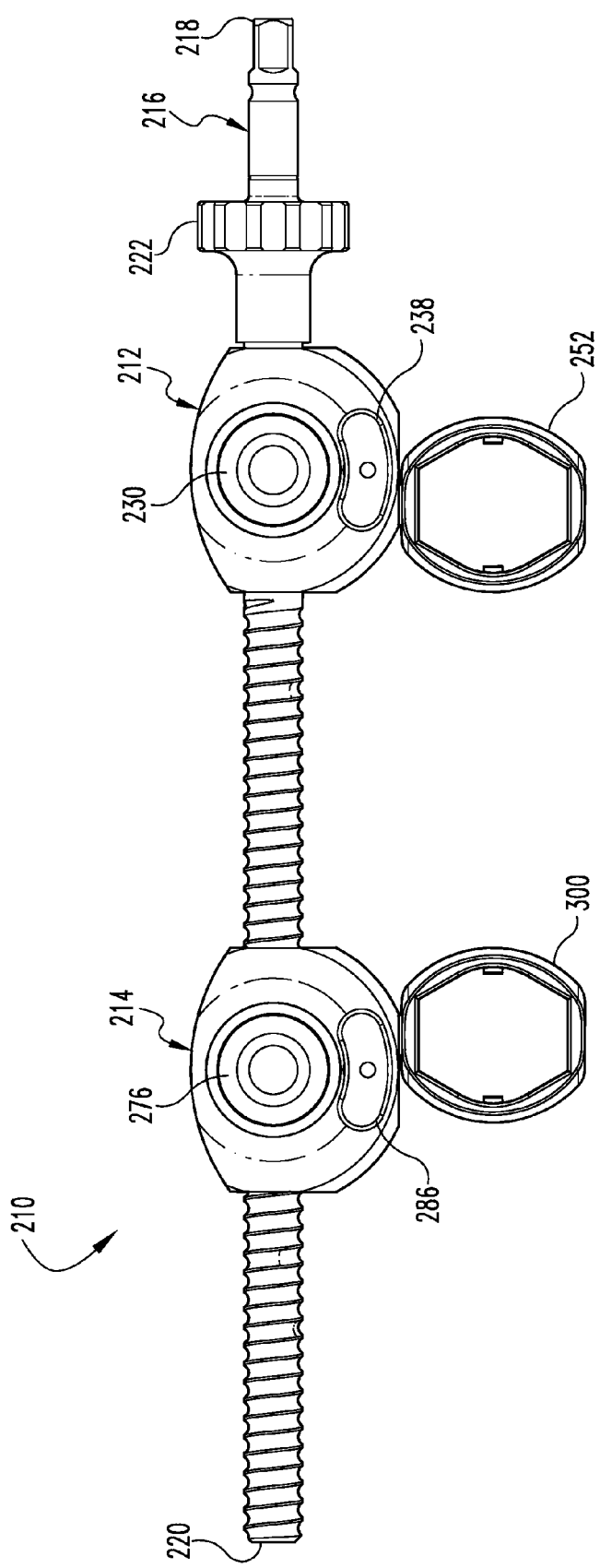
FIG. 6 is a top plan view of a second surgical instrument.

In certain techniques, it should be appreciated that the instrument 10 may be used without other instruments in order to provide a desired orientation of the bones or bony tissues. In other techniques, such as those described below in connection with FIGS. 9-13, the instrument 10 can be used in combination with other instruments to achieve the desired orientation of the subject bones or bony tissues. More specifically, a separation instrument 210 used in the techniques illustrated in FIGS. 9-13 will now be described in connection with FIGS. 6-8.

The instrument 210 generally includes a first end member 212 and a second end member 214 that is movable relative to the first end member 212 along a displacement member 216. The first end member includes a passage (not shown) through which the displacement member 216 is positioned. The displacement member 216 generally extends between a first end 218 and a second end 220. In the illustrated form, the first end 218 has a generally square configuration configured to facilitate engagement with one or more other surgical instruments, one non-limiting example of which includes a driver instrument. In other non-illustrated forms, it is contemplated that the first end 218 could be provided with a round or circular configuration and/or otherwise not be configured to facilitate engagement with any other surgical instruments.

The displacement member 216 also includes a handle member 222, a reduced diameter portion (not shown) similar to the reduced diameter portion 32 discussed above in connection with the displacement member 24, and an externally threaded portion 224. In the illustrated form, the externally threaded portion 224 extends along a portion of the displacement member 216 from the second end 220 toward the first end 218. In addition, the handle member 222 is positioned adjacent to the first end 218 and is generally configured for engagement by a user to facilitate rotation of the displacement member 216. The reduced diameter portion is positioned between the handle member 222 and the externally threaded portion 224 such that it is positioned in the first end member 212 when the displacement member 216 is positioned in the passage of the first end member 212. More particularly, when the displacement member 216 is positioned in the passage, the reduced diameter portion is generally aligned with a transverse bore 226 that extends in communication with the passage. The transverse bore 226 is generally configured to receive a biasing member 228 and a coupling member 230 that is configured to couple the first end member 212 with the displacement member 216. More particularly, the coupling member 230 generally includes a passage 232 that has an upper portion 234 and a lower portion 236 having a reduced profile relative to the upper portion 234. In this arrangement, the upper portion 234 is generally configured to allow the displacement member 216 to freely slide through the coupling member 230, while the lower portion 236 is generally configured to engage with the reduced diameter portion of the displacement member 216 to prevent movement of the displacement member 216 through the coupling member 230.

It should be appreciated that the biasing member 228 normally biases the coupling member 230 away from the first end member 212 such that the lower portion 236 engages with the reduced diameter portion of the displacement member 216. In this arrangement, engagement of the lower portion 236 with the reduced diameter portion of the displacement member 216 axially fixes the displacement member 216 relative to the first end member 212 while allowing rotation of the displacement member 216 relative to the first end member 212. Similarly, when the displacement member 216 is engaged by the coupling member 230, rotation of the handle member 222 will result in rotation of the displacement member 216, including the externally threaded portion 224, relative to the first end member 212. If necessary, the coupling member 230 can be depressed to overcome the force of the biasing member 228 such that the upper portion 234 of the passage 232 of the coupling member 230 receives the displacement member 216 in order to allow removal of the displacement member 216 from the first end member 212.

Figure 7:
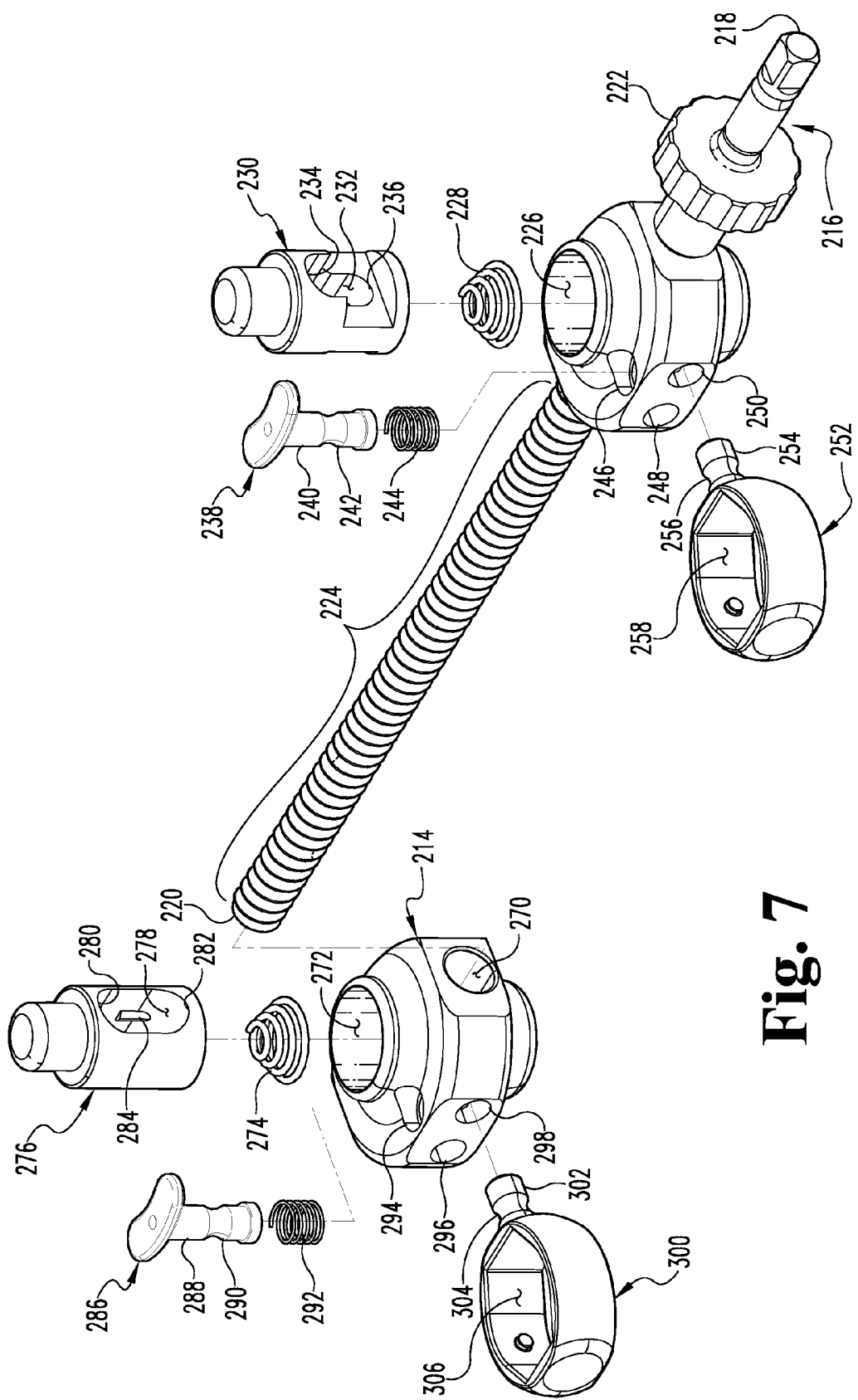
FIG. 7 is an exploded perspective view of the instrument illustrated in FIG. 6.

The second end member 214 generally includes a passage 270 configured to receive a portion of the externally threaded portion 224 of the displacement member 216. The second end member 214 also includes a receptacle 272 through which the passage 270 transversely extends. The receptacle 272 generally receives a biasing member 274 which, in the illustrated form, is a coil spring. However, it should be appreciated that other configurations for the biasing member 274 are contemplated. The receptacle 272 also receives an engaging member 276 that is selectively engageable with the externally threaded portion 224 of the displacement member 216. More specifically, the engaging member 276 includes an elongated passage 278 that includes an upper portion 280 positioned opposite a lower portion 282, as shown in FIG. 7. The upper portion 280 generally does not engage with the displacement member 216 when positioned in the upper portion 280 in order to facilitate passage of the displacement member 216 therethrough. When the externally threaded portion 224 of the displacement member 216 is positioned in the upper portion 280 of the passage 278, the engaging member 276 will generally be freely movable along the longitudinal axis of the displacement member 216. In contrast to the upper portion 280, the lower portion 282 of the passage 278 includes a plurality of rounded projections 284 (only one of which is shown in FIG. 7) that are configured similar to the projections 92a-c of the engaging member 88 and to engage with the externally threaded portion 224 of the displacement member 216 when positioned in the lower portion 282 of the passage 278. When the externally threaded portion 224 of the displacement member 216 is positioned in the lower portion 282 of the passage 278, rotation of the displacement member 216 will result in displacement of the second end member 214 along the longitudinal axis of the displacement member 216.

In its normal operating configuration, the biasing member 274 generally forces the engaging member 276 away from the second end member 214 such that the externally threaded portion 224 of the displacement member 216 is positioned in the lower portion 282 of the passage 278 of the engaging member 276. In this arrangement, the rounded projections 284 engage with the externally threaded portion 224, and the distance between the first and second end members 212, 214 can be adjusted by rotating the displacement member 216. However, a user may also engage the engaging member 276 to depress the biasing member 274 such that the externally threaded portion 224 of the displacement member 216 is positioned in the upper portion 280 of the passage 278 of the engaging member 276, and the second end member 214 can be freely moved along the displacement member 216 without rotation of the displacement member 216. Once a desired relationship between the first and second end members 212, 214 has been obtained, the engaging member 276 can be released such that the externally threaded portion 224 is again positioned in the lower portion 282 and engaged by the rounded projections 284, thereby preventing displacement of the first and second end members 212, 214 relative to one another unless the displacement member 216 is rotated.

Figure 8:
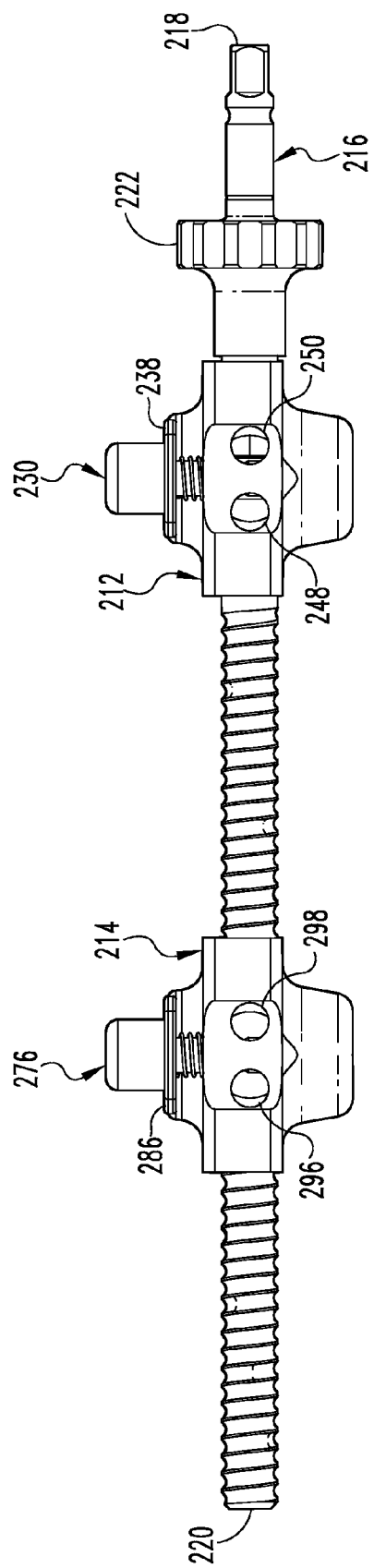
FIG. 8 is a side view of the instrument illustrated in FIG. 6.

It should be appreciated that each of the first and second end members 212, 214 also includes a mounting member 252, 300, respectively, generally configured to facilitate engagement with an anchor extender or other instrument that is engaged with a bone anchor. With further regard to the mounting member 252, it generally includes a hollow interior 258 configured to receive a proximal end of the anchor extender or another instrument engaged with the bone anchor. The mounting member 252 also includes a stem 254 extending therefrom in which a concave, radial groove 256 is formed. As illustrated in FIGS. 7-8, the first end member 212 includes apertures 248, 250 which generally face in a lateral direction such that they are generally transversely oriented relative to the longitudinal axis of the displacement member 216. The apertures 248, 250 are configured to receive the stem 254. In this arrangement, the position of the mounting member 252 relative to the first end member 212 can be changed by moving the stem 254 between the apertures 248, 250. Further, when the mounting member 252 is coupled with the first end member 212, the stem 254 is rotatable within the apertures 248, 250 such that the mounting member 252 can be rotated relative to the first end member 212 as appropriate for engagement with an anchor extender or another instrument.

The first end member 212 is also provided with a release member 238 that includes a stem 240 having a concave, radial groove 242 formed therein. The first end member 212 also includes a receptacle 246 configured to receive the stem 240 and a biasing element 244. In this arrangement, the release member 238 is normally biased relative to the first end member 212 such that the groove 242 is generally positioned above the apertures 248, 250. Similarly, when the mounting member 252 is engaged with the first end member 212 and the stem 254 is positioned in one of the apertures 248, 250, the mounting member 252 will be retained in engagement with the first end member 212 by the release member 238. However, if it is desired to change the position of the mounting member 252 relative to the first end member 212, the release member 238 can be depressed such that the radial groove 256 is brought into alignment with the apertures 248, 250. Once positioned in this manner, the groove 242 will become aligned with the groove 256 on the stem 254 and allow the mounting member 252 to be removed from the first end member 212. The mounting member 252 can then be moved to a different one of the apertures 248, 250 to reengage the mounting member 252 with the first end member 212. Once the mounting member 252 is reengaged with the first end member 212, the release member 238 can be released such that it is again biased away from the first end member 212 with the groove 242 being positioned above the apertures 248, 250 in order to prevent removal of the mounting member 252 from the first end member 212.

The mounting member 300 generally includes a hollow interior 306 configured to receive a proximal end of the anchor extender or another instrument engaged with a bone anchor. The mounting member 300 also includes a stem 302 extending therefrom in which a concave, radial groove 304 is formed. As illustrated in FIGS. 7-8, the second end member 214 includes apertures 296, 298 which generally face in a lateral direction such that they are generally transversely oriented relative to the longitudinal axis of the displacement member 216. The apertures 296, 298 are configured to receive the stem 302. In this arrangement, the position of the mounting member 300 relative to the second end member 214 can be changed by moving the stem 302 between the apertures 296, 298. Further, when the mounting member 300 is coupled with the second end member 214, the stem 302 is rotatable within the apertures 296, 298 such that the mounting member 300 can be rotated relative to the second end member 214 as appropriate for engagement with an anchor extender or another instrument.

The second end member 214 is also provided with a release member 286 that includes a stem 288 having a concave, radial groove 290 formed therein. The second end member 214 also includes a receptacle 294 configured to receive the stem 288 and a biasing element 292. In this arrangement, the release member 286 is normally biased relative to the second end member 214 such that the groove 290 is generally positioned above the apertures 296, 298. Similarly, when the mounting member 300 is engaged with the second end member 214 and the stem 302 is positioned in one of the apertures 296, 298, the mounting member 300 will be retained in engagement with the second end member 214 by the release member 286. However, if it is desired to change the position of the mounting member 300 relative to the second end member 214, the release member 286 can be depressed such that the radial groove 290 is brought into alignment with the apertures 296, 298. Once positioned in this manner, the groove 290 will become aligned with the groove 304 on the stem 302 and allow the mounting member 300 to be removed from the second end member 214. The mounting member 300 can then be moved to a different one of the apertures 296, 298 to reengage the mounting member 300 with the second end member 214. Once the mounting member 300 is reengaged with the second end member 214, the release member 286 can be released such that it is again biased away from the second end member 214 with the groove 290 being positioned above the apertures 296, 298 in order to prevent removal of the mounting member 300 from the second end member 214.

Figure 9:
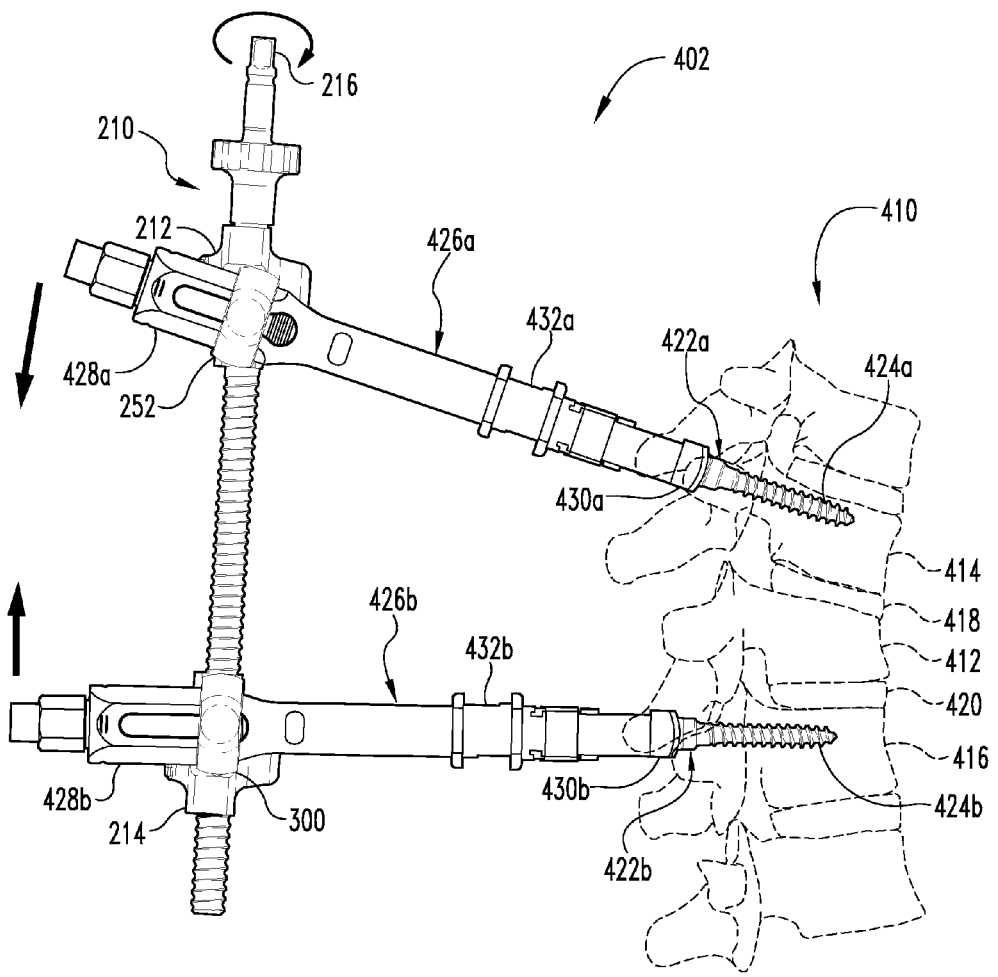
FIGS. 9-11 illustrate one technique for adjusting the relative positioning of vertebrae using the instruments illustrated in FIGS. 1 and 6.
Figure 10:
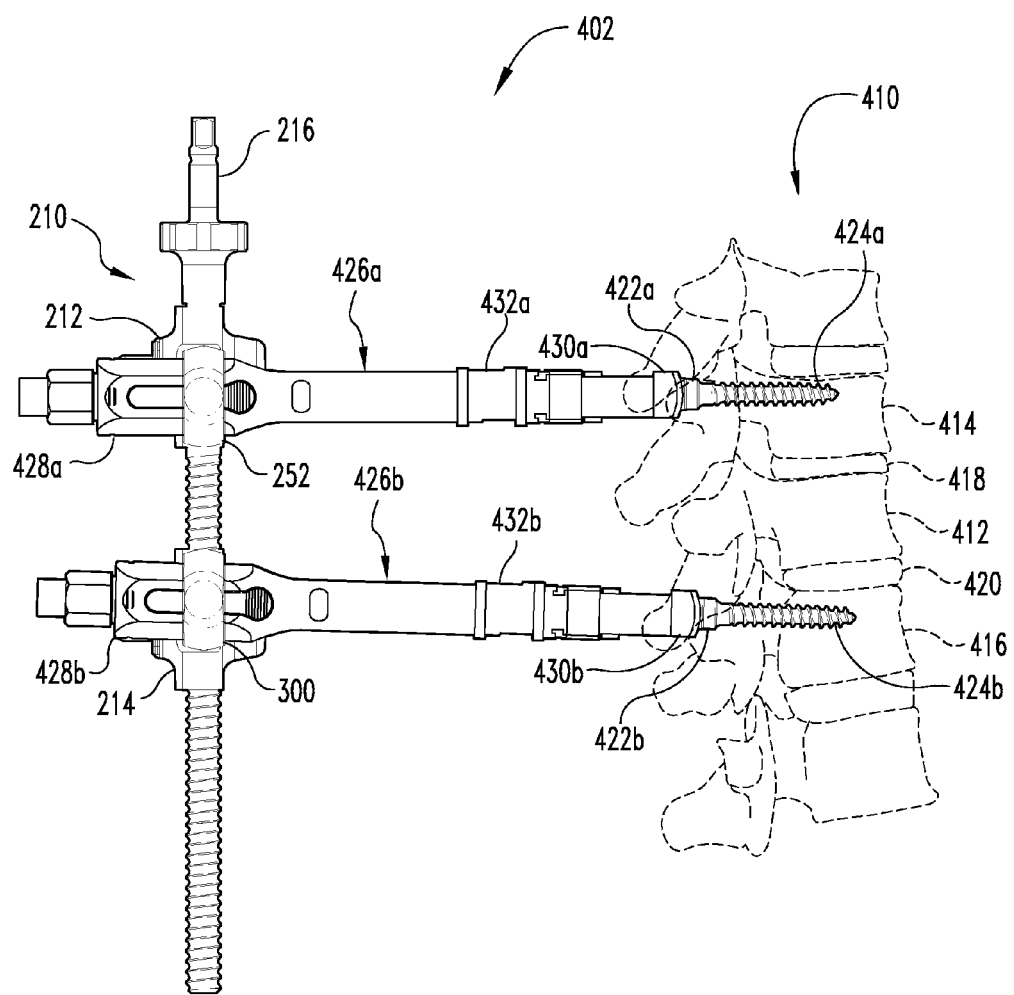
Figure 11:
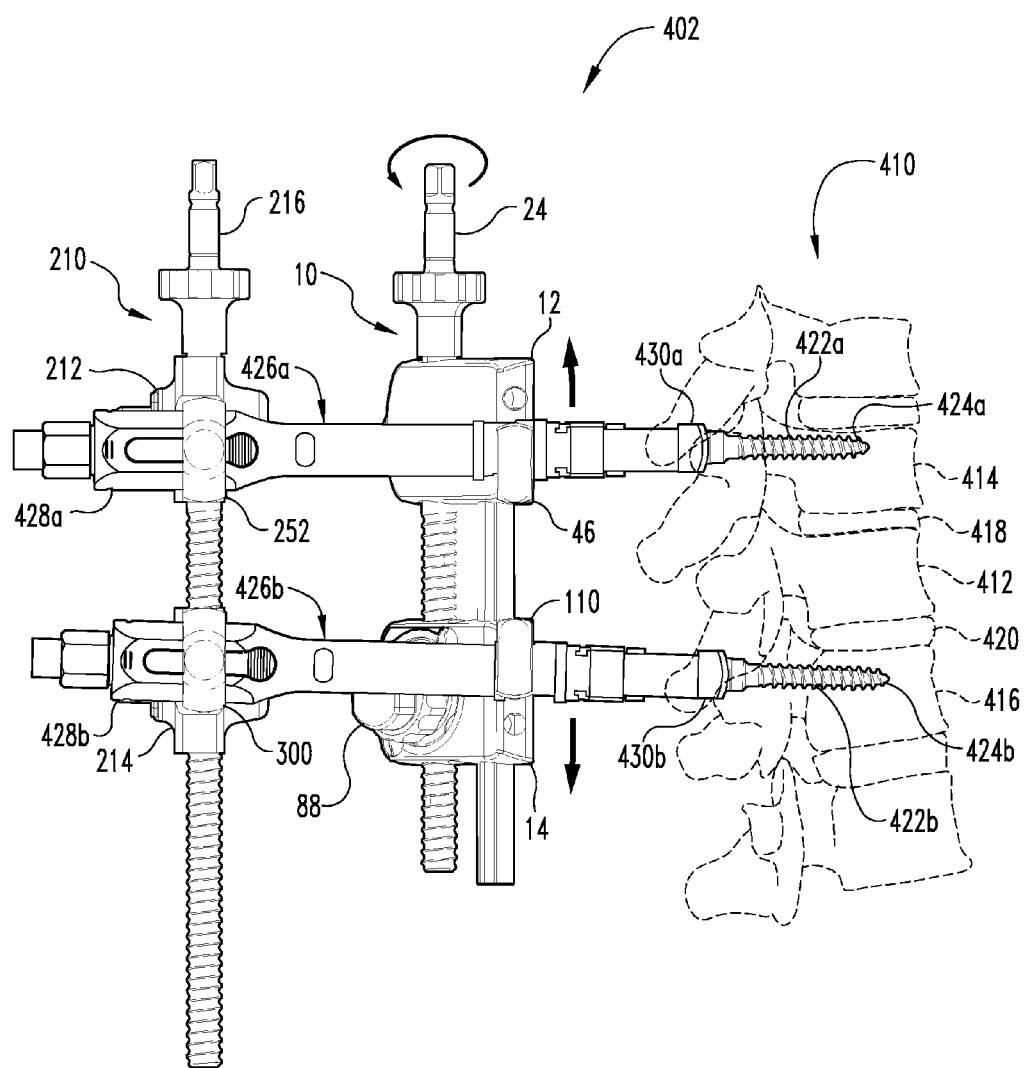
Figure 12:
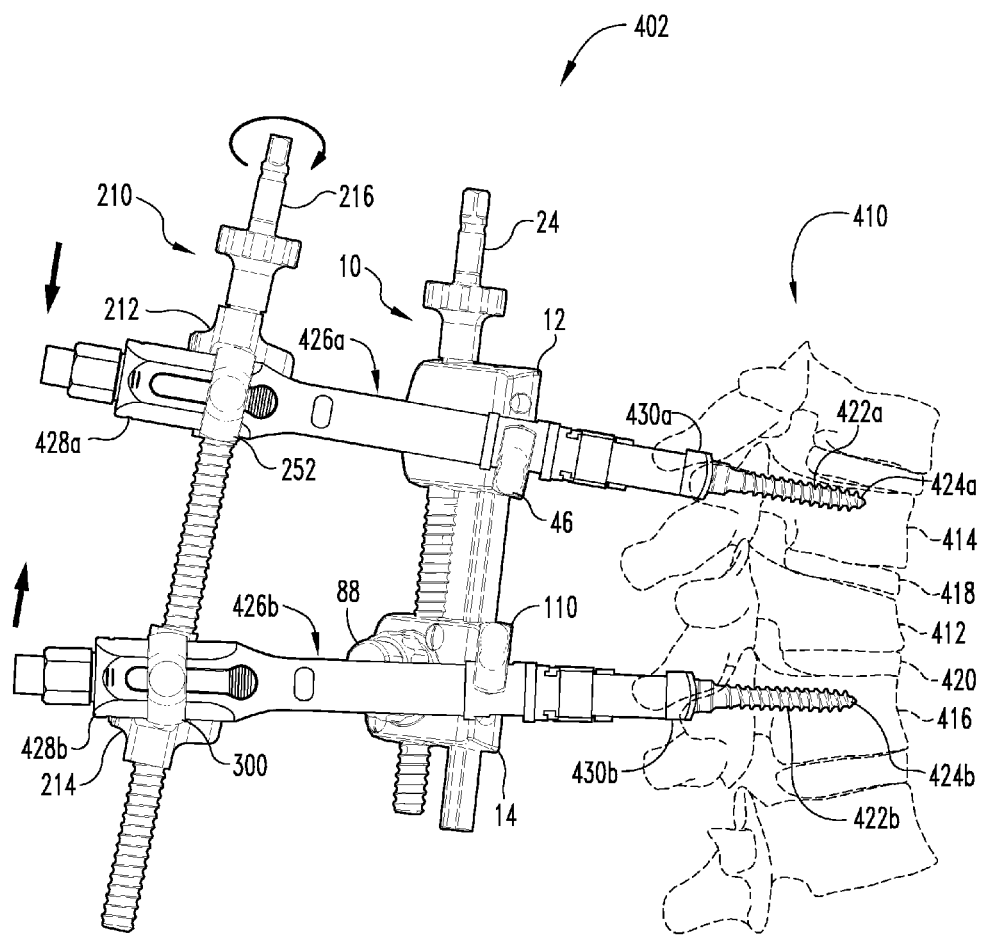
FIGS. 12-13 illustrate an alternative technique for adjusting the relative positioning of vertebrae using the instruments illustrated in FIGS. 1 and 6.
Figure 13:
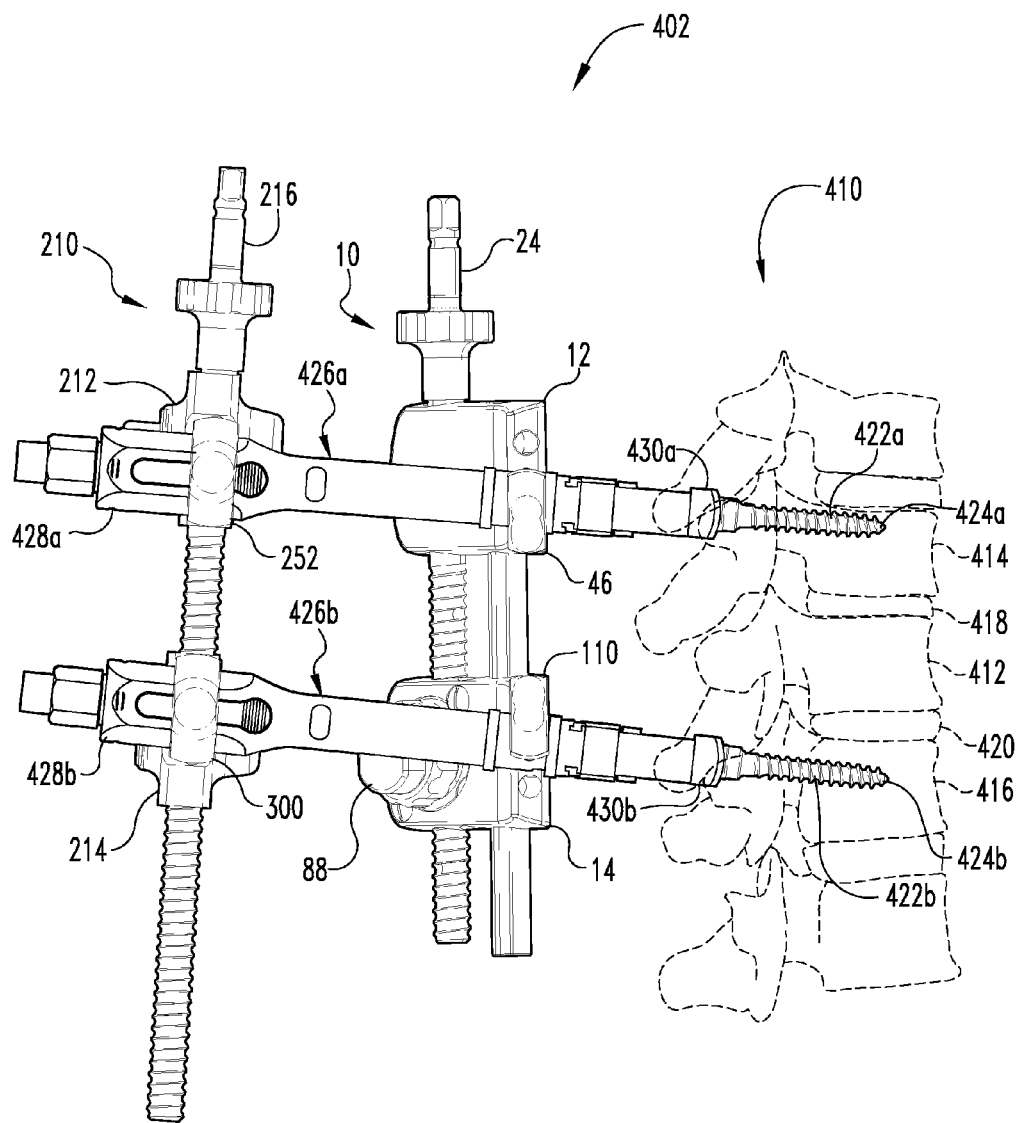

Referring now to FIGS. 9-11, illustrated therein are further details regarding a system 402 in which the instruments 10, 210 are utilized in combination with one another. More particularly, the technique described in connection with FIGS. 9-11 may be used to adjust alignment of the spinal column when a vertebra having an anterior fracture or defect is present, although use of this technique for adjusting alignment of the spinal column due to other deformities is also contemplated. Referring to FIG. 9, there is illustrated a segment of the spinal column 410 including a damaged vertebra 412 positioned between vertebrae 414 and 416. An intervertebral disc 418 extends between vertebrae 412 and 414, and an intervertebral disc 420 extends between vertebrae 412 and 416. Access to the vertebrae 412, 414, 416 may be performed using a posterior, posterolateral or other approach known to those skilled in the art. Once access to the vertebrae 412, 414, 416 has been obtained, bone anchors 422a, 422b are engaged with the vertebrae 414, 416, respectively. The bone anchors 422a, 422b generally include proximal receiving portions configured to receive a connecting element (not shown) and a distal bone engaging portion 424a, 424b. In the illustrated embodiment, bone engaging portions 424a, 424b are bone screws including a threaded shank to engage the bony structure of the underlying vertebrae 414, 416. The proximal receiving portions are configured as receivers having a pair of opposing arms defining a longitudinal passage. The arms further define a proximal/distally extending opening that opens at a proximal end of the arms to receive a set screw (not shown) to secure the connecting element in the passage. Bone engaging portions 424a, 424b can be pivotally received in the proximal receiving portions through the distal openings thereof, and structured to interact therewith to provide the bone anchors 422a, 422b with multi-axial capabilities that permit either a select number of positions or an infinite number of positions of bone engaging portions 424a, 424b relative to the proximal receiving portions.

Other forms for the bone anchors 422a, 422b are also contemplated, including uni-axial and uni-planar forms. The bone engaging portion can also be in the form of a spike, staple, hook, fusion device, cannulated screw, fenestrated screw, interbody device, intrabody device, clamp, plate, suture anchor, bolt, pin or other bone engaging member. The receiving portion can be in the form of a saddle, yoke, eye-bolt or through-hole, side opening member, bottom opening member, top-opening member, eyelet, or any other structure engageable to connecting element 40.

The system 402 also includes anchor extenders 426a, 426b which each extend between a proximal end portion 428a, 428b and a distal end portion 430a, 430b, and include a mounting portion 432a, 432b positioned between the proximal and distal end portions 428a, 428b and 430a, 430b configured to facilitate engagement with the instrument 10. Furthermore, the distal end portions 430a, 430b are generally configured to facilitate releasable engagement of the anchor extenders 426a, 426b with the bone anchors 422a, 422b. While not intending to be limited to any particular configuration, further details regarding the general structure and function of one non-limiting form for the anchor extenders 426a, 426b are provided in U.S. Patent Application Publication No. 2008/0319477 to Justis et al., the contents of which are incorporated herein by reference in their entirety. However, it should be appreciated that alternatively configured anchor extenders are also contemplated for use with the system 402.

As illustrated in FIG. 9, once the anchor extenders 426a, 426b have been engaged with the bone anchors 424a, 424b, the instrument 210 can be coupled with the anchor extenders 426a, 426b by positioning the mounting members 252, 300 on the proximal end portions 428a, 428b. If necessary, one or both of the mounting members 252, 300 can be rotated relative to the end members 212, 214, respectively, in order to facilitate positioning on the proximal end portions 428a, 428b. Once the instrument 210 has been coupled with the anchor extenders 428a, 428b, the displacement member 216 can be rotated to bring the first and second end members 212, 214, and the proximal end portions 428a, 428b with which they are engaged, toward one another, as indicated by the directional arrows in FIG. 9. As the proximal end portions 428a, 428b are brought toward one another, the vertebrae 414, 416 are rotated about the vertebra 412 until a desired alignment of the vertebrae 412, 414, 416 is achieved, as illustrated in FIG. 10.

It should be appreciated that rotation of the vertebrae 414, 416 about the vertebra 412 in the manner described above can result in compression of a posterior portion of one or both of the discs 418, 420. As a result, the desired spacing between the vertebrae 412, 414 and the vertebrae 412, 416 along their posterior portions must be established. Similarly, in order to achieve this desired spacing, the instrument 10 is coupled with the anchor extenders 426a, 426b by positioning the hook portions 46, 110 on the mounting portions 432a, 432b. Once the instrument 10 is engaged with the anchor extenders 426a, 426b, the displacement member 24 can be rotated to move the first and second end members 12, 14 away from one another, as indicated by the directional arrows in FIG. 11. As the first and second end members 12, 14 are moved in this manner, a distraction force is applied to the bone anchors 422a, 422b through the anchor extenders 426a, 426b such that the vertebrae 414, 416 are moved away from the vertebra 412 until a desired spacing therebetween is achieved. After the desired orientation and spacing between the vertebrae 412, 414, 416 has been achieved, a connecting element (not shown) can be positioned and locked in the proximal receiving portions of the bone anchors 422a, 422b to maintain the desired orientation and spacing, and the instruments 10, 210 and the anchor extenders 426a, 426b can be removed from the surgical site.

Other techniques using the system 402 are also contemplated. For example, one such alternative technique will be described in connection with FIGS. 12-13. In one form, this alternative technique may be used when, for example, excessive compression of the posterior portion of one or more of the vertebrae 412, 414, 416 must be avoided due to certain deformities, such as a fracture of the posterior wall of one or more of the vertebrae 412, 414, 416. In this technique, the instruments 10, 210 will generally be engaged with the anchor extends 426a, 426b at or very near the same time. Once the instruments 10, 210 have been engaged with the anchor extenders 426a, 426b, the displacement member 216 can be rotated to bring the first and second end members 212, 214 of the instrument 210 toward one another, as indicated by the directional arrows in FIG. 12. As the first and second end members 212, 214 are brought toward one another, the instrument 10 generally maintains spacing of the anchor extenders 426a, 426b relative to one another at the mounting portions 432a, 432b such that the anchor extenders 426a, 426b are pivoted about the instrument 10, which in turn changes the alignment of the vertebrae 214, 216 relative to the vertebra 212. The displacement member 24 of the instrument 10 can also be rotated to change the relative positioning of the first and second end members 12, 14 during the surgical procedure in order to obtain a desired spacing of the vertebrae 212, 214 and 212, 216 and/or to adjust pivoting of the anchor extenders 426a, 426b relative to the instrument 10. As discussed above, once the desired orientation and spacing between the vertebrae 412, 414, 416 has been obtained, a connecting element (not shown) can be positioned and locked in the proximal receiving portions of the bone anchors 422a, 422b to maintain the desired orientation and spacing, and the instruments 10, 210 and the anchor extenders 426a, 426b can be removed from the surgical site.

It should be appreciated that use of the system 402 on immediately adjacent vertebrae and/or vertebrae separated by more than one intermediate vertebra are contemplated. In addition, the instruments 10, 210 and/or the system 402 may also be used at other anatomical locations besides the spinal column. It should also be appreciated that the instruments 10, 210 can be used in surgical procedures independent of one another and/or without the anchor extenders 426a, 426b. For example, in one non-limiting form, it is contemplated that the hook portions 46, 110 of the instrument 10 can be directly engaged with the bones or bony tissues which are targeted for movement by the instrument 10. Once engaged therewith, the displacement member 24 can be rotated in order to change the relative positioning of the first and second members 12, 14 to provide compression or distraction to the bones or bony tissues.

It should be appreciated that, unless otherwise described, the instruments 10, 210 and other components of the system 402 described herein may be made from any suitable biocompatible material, including but not limited to titanium, titanium alloy, stainless steel, metallic alloys, polyaryletherketone (PAEK), polyetheretherketone (PEEK), carbon-reinforced PEEK, polyetherketoneketone (PEKK), polysulfone, polyetherimide, polyimide, ultra-high molecular weight polyethylene (UHMWPE), and plastics, just to name a few possibilities. Further, it should also be appreciated that the instruments, devices, systems, techniques and methods described herein may also be used in surgical procedures involving animals, or in demonstrations for training, education, marketing, sales and/or advertising purposes. Furthermore, the instruments, devices, systems, techniques and methods described herein may also be used on or in connection with a non-living subject such as a cadaver, training aid or model, or in connection with testing of surgical systems, surgical procedures, orthopedic devices and/or apparatus.

Any theory, mechanism of operation, proof, or finding stated herein is meant to further enhance understanding of the present application and is not intended to make the present application in any way dependent upon such theory, mechanism of operation, proof, or finding. It should be understood that while the use of the word preferable, preferably or preferred in the description above indicates that the feature so described may be more desirable, it nonetheless may not be necessary and embodiments lacking the same may be contemplated as within the scope of the application, that scope being defined by the claims that follow. In reading the claims it is intended that when words/phrases such as "a", "an", "at least one", and/or "at least a portion" are used, there is no intention to limit the claim to only one item unless specifically stated to the contrary in the claim. Further, when the language "at least a portion" and/or "a portion" is used, the item may include a portion and/or the entire item unless specifically stated to the contrary.

While the application has been illustrated and described in detail in the drawings and foregoing description, the same is to be considered as illustrative and not restrictive in character, it being understood that only the selected embodiments have been shown and described and that all changes, modifications and equivalents that come within the spirit of the application as defined herein or by any of the following claims are desired to be protected.

What is claimed is:

1. An instrument for adjusting relative positioning of at least two vertebrae, comprising:
  a first end member including a guide bar and a displacement member extending therefrom, said displacement member includes an externally threaded portion;
  a second end member configured to engage with said guide bar and said displacement member, said second end member further including an engaging member selectively engageable with said displacement member,
  said engaging member includes an elongated passage in which a portion of said externally threaded portion is received, said elongated passage including an upper portion and a lower portion including a plurality of rounded projections configured to engage with threading of said externally threaded portion when said engaging member is engaged with said displacement member,
  said second end member further includes a biasing member configured to normally bias said engaging member into engagement with said displacement member such that said plurality of rounded projections engage with said threading and prevent displacement of said second end member relative to said first end member without rotation of said displacement member; and
  wherein said second end member is movable relative to said first end member along said guide bar and said displacement member upon rotation of said displacement member relative to said first end member when said engaging member is engaged with said displacement member and independent of rotation of said displacement member relative to said first end member when said engaging member is disengaged from said displacement member.

2. The instrument of claim 1, wherein said biasing member is compressible to facilitate displacement of said engaging member relative to said displacement member such that said displacement member is positioned in said upper portion of said elongated passage and said engaging member is disengaged from said displacement member.

3. The instrument of claim 2, wherein said upper portion of said elongated passage is configured to provide clearance around said displacement member such that said second end member is freely movable along said displacement member relative to said first end member when said displacement member is in said upper portion of said elongated passage.

4. The instrument of claim 1, wherein each of said first and second end members includes an open-sided hook portion configured to receive and engage with a portion of a respective one of first and second anchor extenders.

5. The instrument of claim 4, wherein each of said open-sided hook portions is selectively rotatable relative to a respective one of said first and second end members.

6. The instrument of claim 1, wherein said displacement member is axially fixed relative to said first end member.

7. An instrument for adjusting relative positioning of at least two vertebrae, comprising:
a first end member and a second end member, said second end member is axially displaceable relative to said first end member, said first and second end members each including a hook member including an engaging portion engaged with a respective one of a first anchor extender and a second anchor extender,
wherein each of said hook members is selectively rotatable relative to a respective one of said first and second end members from a first position wherein said engaging portions face toward one another to a second position wherein said engaging portions face away from one another,
wherein each of said first and second end members further includes a locking member configured to selectively retain said hook members in a respective one of said first position and said second position,
wherein each of said first and second end members includes a center aperture and a pair of lateral apertures positioned on opposite sides of said center aperture; each of said hook members includes first and second stems extending therefrom; and said first stems are received in said center apertures and said second stems are received in a first one of said lateral apertures when said hook members are in said first position and a second one of said lateral apertures when said hook members are in said second position.

8. The instrument of claim 7, wherein each of said locking members is normally biased into engagement with a respective one of said second stems of said first and second hook members.

9. The instrument of claim 8, wherein each of said hook members is releasable from a respective one of said first and second end members upon disengagement of said locking members from said second stems.

10. The instrument of claim 7, wherein said first end member includes a guide bar and a displacement member extending therefrom, and said second end member is engaged with and axially displaceable along said guide bar and said displacement member.

11. The instrument of claim 10, wherein each of said hook members extends obliquely to said guide bar and said displacement member.

12. A system for adjusting relative positioning of at least two vertebrae, comprising:
a first anchor extender extending between a proximal end and a distal end configured to engage with a first bone anchor;
a second anchor extender extending between a proximal end and a distal end configured to engage with a second bone anchor;
a first instrument including a first end member engageable with said proximal end of said first anchor extender and a second end member engageable with said proximal end of said second anchor extender,
wherein said second end member is selectively movable relative to said first end member to change a distance between said proximal ends of said anchor extenders;
and a second instrument including a first end member and a second end member selectively movable relative to said first end member to change a distance between said first and second end members, wherein said second instrument is engageable with said first and second anchor extenders at a location between said proximal and distal ends.

13. The system of claim 12, wherein said first and second end members of said second instrument each include a hook member including an engaging portion configured to engage with a respective one of said first and second anchor extenders, said hook members each being selectively rotatable relative to a respective one of said first and second end members from a first position wherein said engaging portions face toward one another to a second position where said engaging portions face away from one another.

14. The system of claim 12, wherein said second end member of said second instrument further includes an engaging member selectively engageable with a displacement member extending from said first end member, and said second end member is movable relative to said first end member upon rotation of said displacement member relative to said first end member when said engaging member is engaged with said displacement member and independent of rotation of said displacement member relative to said first end member when said engaging member is disengaged from said displacement member.

* * * * *